United States Patent [19]
Burmeister et al.

[11] Patent Number: 5,395,965
[45] Date of Patent: Mar. 7, 1995

[54] CATALYST FOR THE PRODUCTION OF A GLYOXYLIC ACID BY CATALYTIC OXIDATION OF GLYOXAL AND METHOD OF ITS PRODUCTION

[75] Inventors: Roland Burmeister, Hanau; Klaus Deller, Hainburg, both of Germany; Bertrand Despeyroux, Fourqueux; Hatté Christine, Camon, both of France

[73] Assignee: Degussa Aktiengesellschaft, Frankfurt am Main, Germany

[21] Appl. No.: 246,402

[22] Filed: May 20, 1994

[30] Foreign Application Priority Data

Jul. 21, 1993 [DE] Germany ............... 43 24 442.4

[51] Int. Cl.⁶ ............... B01J 21/18; C07C 59/00; C07C 51/00; C07C 59/153
[52] U.S. Cl. ............... 562/531; 562/577; 502/185
[58] Field of Search ............... 562/531, 577; 502/185

[56] References Cited

U.S. PATENT DOCUMENTS

| | | | |
|---|---|---|---|
| 4,970,128 | 11/1990 | Itoh et al. | 429/42 |
| 5,096,866 | 3/1992 | Itoh | 502/101 |
| 5,171,884 | 12/1992 | de Mesantourne et al. | 562/531 |
| 5,214,184 | 5/1993 | Matuzaki et al. | 558/277 |

FOREIGN PATENT DOCUMENTS 0438948  7/1991  European Pat. Off. .

*Primary Examiner*—Arthur C. Prescott
*Attorney, Agent, or Firm*—Beveridge, DeGrandi, Weilacher & Young

[57] ABSTRACT

A catalyst containing platinum on carbon as carrier for the catalytic oxidation of glyoxal to glyoxalic acid. Activity and selectivity of the catalyst can be considerably improved by modification with molybdenum and/or cerium.

4 Claims, No Drawings

CATALYST FOR THE PRODUCTION OF A GLYOXYLIC ACID BY CATALYTIC OXIDATION OF GLYOXAL AND METHOD OF ITS PRODUCTION

INTRODUCTION AND BACKGROUND

The present invention relates to a catalyst containing platinum on a carbon carrier for the catalytic oxidation of glyoxal to provides glyoxylic acid with good activity, selectivity and yield. In another aspect, the present invention relates to the method of producing the catalyst and the method of making glyoxylic acid.

Glyoxylic acid is obtained on an industrial scale by means of the oxidation of glyoxal with strong acids such as nitric acid. Electrochemical methods are also described in the literature.

EP 0,438,948 A1 describes the direct catalytic oxidation of glyoxal by means of heterogeneous carrier catalysts to glyoxylic acid. In example 1 of this patent a optimized catalyst is prepared in that at first the activated carbon carrier is partially burned after an HCl wash at 500° C. in a current of air, which results in an elevation of its specific carrier surface. This is followed by impregnating the carrier treated in this manner with an aqueous solution of hexachloroplatinic acid, treating with formaldehyde, converting with potassium hydroxide and subsequently washing and drying. The catalyst obtained in this manner exhibits a homogeneous distribution of platinum particles in a range of 1.5 to 2 nm.

The catalyst produced according to EP 0,438,948 and containing 4.2% platinum when used in the catalytic oxidation of glyoxal results in a yield of 73% and a selectivity of 79.3% of glyoxylic acid. The ratio of catalyst to glyoxal used in the reference is indicated at about 43% by weight. A catalytic activity of 1.24 mmoles glyoxylic acid per mmole platinum per minute can be calculated for the reaction time of 110 minutes indicated in example 1 of EP 0,438,948.

The partial combustion of the activated carbon carrier and the further steps of the preparation of the catalyst are apparently essential for the effective utilization of the platinum-containing, catalytically active phases of EP 0,348,948.

Unfortunately, decisive steps for the production of the catalyst can not be reproduced from the art. Although the partial combustion of the activated carbon is an essential step of this catalytic preparation, any indication of the amount required as well as of the resulting quantity of activated carbon obtained after partial burning is lacking for this. In addition, it has been found that many steps of this catalytic preparation are very complicated. For example, the conversion of the activated carbon with nitric acid is carried out for 24 hours.

One of the objects of the present invention is to provide a catalyst for the oxidation of glyoxal to produce glyoxylic acid which is distinguished from the catalysts of the state of the art by a lower noble metal requirement and an improved economy resulting therefrom. A further object of the present invention concerns a method of producing this catalyst.

SUMMARY OF THE INVENTION

In achieving the above and other objects, one feature of the invention resides in a catalyst containing platinum on a carbon carrier for the catalytic oxidation of glyoxal to form glyoxylic acid.

Described in greater detail, the catalyst of this invention comprises, in addition to the platinum, molybdenum and/or cerium in addition as modifiers. The platinum is present, relative to the carrier, in an amount of 0.1 to 5, preferably 0.5 to 3.5% by weight and the weight ratio between the platinum and the molybdenum and/or cerium component which is present at the same time is 1:1 to 1:20, preferably 1:1 to 1:5. According to the invention, the platinum and molybdenum and/or cerium are finely distributed on the carrier.

The catalyst exhibits especially favorable qualities if the average particle diameter of the activated carbon is 15 to 30 μm, its specific surface is greater than 500 m²/g and its total pore volume is greater than 0.5 ml/g.

A further feature of the present invention is a method for producing a catalyst by means of the simultaneous precipitation of a platinum compound and a molybdenum compound and/or cerium compound onto the carrier of activated carbon, reducing, filtering and washing the product.

Described in greater detail, the method of the invention is carried out by forming an aqueous suspension with 5 to 30% by weight activated carbon. The platinum and additional molybdenum and/or cerium are added to the suspension in the form of a solution of their respective water-soluble compounds. The content of this solution of platinum and molybdenum and/or cerium is measured according to the desired charge of the amount of activated carbon used. The mixture of suspension and solution obtained as above is heated under agitation to 70° to 100° C., in order that platinum and molybdenum and/or cerium in the form of their barely soluble compounds are precipitated simultaneously by means of the addition of a base on the activated carbon. Subsequently, the mixture is reduced at unchanged temperature by the addition of a reducing agent.

DETAILED DESCRIPTION OF THE INVENTION

The catalytic oxidation of glyoxal to glyoxylic acid can be carried out by oxidation of glyoxal with a stream of oxygen in the presence of the catalyst of this invention. Conventional reaction vessels and systems can be used for this purpose.

In making the catalyst of this invention, the platinum and the combined molybdenum and cerium components are used in water soluble forms so that solutions can readily be prepared.

Suitable water-soluble compounds for the production of the catalyst are hexachloroplatinic acid, molybdatophosphoric acid and ceric chloride. Sodium carbonate, sodium hydroxide solution or potash lye can be used as the base for precipitating the metal compounds. Hydrazine, sodium formate, sodium hydridoborate or formaldehyde are suitable for the reduction of the precipitated metal compounds, with formaldehyde being used with preference.

The impregnation of the activated carbon with the metal compounds can take place either as described above by means of the simultaneous precipitation of all metal compounds out of the solution or, sequentially, one after the other. In the case of a separate precipitation the activated carbon is preferably impregnated at first with platinum and in a second process step with the molybdenum salts and/or ceric salts.

In the following examples 1 to 6 of the invention and comparative examples 1 to 4 the performance data of a few catalysts in accordance with the invention and of comparative catalysts representative of the state of the art were determined in the catalytic oxidation of glyoxal to glyoxylic acid. The measured performance data of the catalysts concerned conversion, selectivity, yield and activity.

Oxalic acid, glycolic acid and other byproducts are produced during the catalytic oxidation of glyoxal in addition to the desired product (glyoxylic acid) as peroxidation products. The concentration of glyoxylic acid in the reaction solution at first increases with rising reaction time and falls after having passed through a maximum on account of overoxidation of the already formed glyoxylic acid to oxalic acid. The concentration of the undesired byproducts, especially of the oxalic acid, increases with increasing reaction time.

Conversion, selectivity, yield and activity were therefore determined for the time of maximum concentration of glyoxylic acid in accordance with the following definition equations:

$$\text{Conversion} = \frac{\text{amount glyoxal converted (mmole/l)}}{\text{amount glyoxal added (mmole/l)}} \cdot 100\%$$

$$\text{Selectivity} = \frac{\text{amount glyoxylic acid formed (mmole/l)}}{\text{amount glyoxal converted (mmole/l)}} \cdot 100\%$$

$$\text{Yield} = \frac{\text{amount glyoxylic acid formed (mmole/l)}}{\text{amount glyoxal converted (mmole/l)}} \cdot 100\%$$

$$\text{Activity} = \frac{\text{amount glyoxal added (mmole/l)}}{\text{amount platinum added (mmole)} \cdot T_{max} \text{ (min)}}$$

$T_{max}$ designates the reaction time until attainment of the maximum glyoxylic-acid concentration.

Catalytic Production

The same activated carbon was used as the catalytic carrier for the catalysts of the examples and reference examples. It exhibited the following qualities:
Specific surface: 1500 m²/g according to ASTM-D-3663
Total pore volume: 1.5 ml/g according to ASTM-D-4284
Average grain size: 22 μm
Residual ash content: <2%

The type of suitable activated carbon that can be used for purposes of this invention will be readily apparent to those skilled in the art. See Kirk-Othmer, Encyclopedia of Chemical Technology, 3rd Edition, Vol. 4, pages 561 to 569 incorporated herein by reference.

In order to produce the catalysts, an aqueous activated-carbon suspension was first produced. 100 g activated carbon (dry weight), reduced by the weight of the catalytic components to be applied, were stirred in each instance into distilled water. Thus, 95 g activated carbon were used for a Pt/C catalyst with 5% by weight platinum charge.

The quantities of impregnating solutions with the catalytically active components were so determined in such a manner in their concentration and amount that their content of the catalytic components corresponded precisely to the necessary charge of the amount of activated carbon used. Thus, an impregnating solution with a content of 5 g platinum was prepared for producing a 5% by weight Pt/C catalyst.

In the case of catalysts modified with molybdenum or cerium, impregnating solutions were prepared which contained both the platinum precursors as well as the precursors of the modifiers in order to precipitate them in common onto the activated-carbon carrier.

The following precursors were used:

| | | |
|---|---|---|
| for platinum: | hexachloroplatinic acid | $H_2PtCl_6$ |
| for molybdenum: | molybdatophosphoric acid | $H_3P(Mo_3O_{10})_4$ |
| for cerium: | cerium chloride | $CeCl_3$ |
| for lead: | lead acetate | $Pb(CH_3CO_2)_2$ |

Lead was used as modifier in reference example 4.

In order to precipitate the catalytic components onto the activated-carbon carrier the impregnating solutions were stirred into the aqueous activated-carbon suspension previously produced.

The suspension was then heated to 80° C. and 10% sodium hydroxide solution stirred in for precipitating the catalytic components (approximately 75 ml sodium hydroxide solution for 100 g of a catalyst with 5% by weight platinum). The catalytic components were subsequently reduced by means of the addition of a 37% formaldehyde solution (2.5 ml for 100 g catalyst with 5% by weight platinum) while holding the temperature of 80° C. After the reduction the finished catalyst was filtered off via a suction filter and washed with distilled water.

The catalysts were used in a wet state for determining the performance data.

Catalyst Testing

The oxidation of glyoxal to glyoxylic acid was carried out in a 250 ml stirred-tank reactor with gassing (bubble) agitator, thermometer, alkali dosing, pH measuring electrode and oxygen supply.

To this end, 90 ml of an aqueous glyoxal solution with 0.523 g glyoxal (corresponding to 0.1 mole glyoxal/l or 9 mmole glyoxal) together with 0.225 g of the catalyst to be tested were filled in each instance into the reactor. The selected amounts of catalyst and glyoxal required yield the same weight ratios as in example 2 of EP 0,438,948 A1.

The oxygen for the oxidation was distributed by the gassing agitator in the solution. The gas pressure was 10 mbars over normal pressure, the reaction temperature 30° C.

The reaction product glyoxylic acid being produced was continually neutralized by adding in 10% by weight sodium hydroxide solution dropwise. This enabled the pH of the reaction solution to be held constant at a value of 7.7. The course in time of the reaction was followed by means of a regular taking of samples. The samples were analyzed with ion chromatography and HPLC.

The results of the measuring series are listed in table 1. Column 1 indicates the compositions of the catalysts tested. In it, the indication 5% Pt-5% Mo/C, for example, designates a platinum catalyst which is modified with molybdenum and is on activated carbon with 5% by weight platinum and 5% by weight molybdenum. The abbreviation VB designates the comparative examples in accordance with the state of the art whereas the abbreviation B designates the examples of the invention.

Aside from example B6, only 0.225 g catalyst was used. In example B6 the amount of catalyst was increased fivefold, that is, to 1.125 g.

Column 2 indicates the time until attainment of the maximum concentration of glyoxylic acid. The data on conversion, selectivity, yield and activity was determined at this time.

Table 1 shows that the catalysts of examples B1, B2 modified in accordance with the invention with molybdenum exhibit distinctly better selectivities, yields and activities than the reference catalysts of reference examples VB1, VB2.

Reference example VB4 makes it clear that lead is totally unsuitable as a modifer for the reaction observed here even though lead is used in other instances for modifying Pt/C catalysts. The HPLC analysis shows in this instance that the poor activity can be traced back to the fact that glyoxal is further oxidized on this catalyst, preferably to oxalic acid.

Examples B4, B5 and B6 show that catalysts modified with cerium exhibit a considerably improved selectivity in the oxidation of glyoxalic acid to glyoxylic acid.

Further modifications and variations of the invention will be apparent to those skilled in the art from the foregoing and are intended to be encompassed by the claims appended hereto.

German priority application P 43 24 442.4 is relied on and incorporated herein by reference.

preferably 1:1 to 1:5 and that platinum and molybdenum and/or cerium are finely distributed on the carrier.

2. The catalyst according to claim 1, characterized in that the average particle diameter of the activated carbon is 15 to 30 μm, its specific surface is greater than 500 m$^2$/g and its total pore volume is greater than 0.5 ml/g.

3. A method of producing the catalyst according to claim 2 by precipitating a platinum compound onto the carrier of activated carbon, reducing, filtering and washing the product, characterized in that an aqueous suspension with 5 to 30% by weight activated carbon is produced, that platinum and additional molybdenum and/or cerium are added in the form of a solution of their water-soluble compounds to the suspension, that the content of this solution of platinum and molybdenum and/or cerium is measured according to the desired charge of the amount of activated carbon used, that this mixture of suspension and solution is heated under agitation to 70° to 100° C., that platinum and molybdenum and/or cerium are precipitated in the form of their poorly soluble compounds simultaneously by means of the addition of a base on the activated

TABLE 1

| Example | $T_{max}$ (min) | Conversion (%) | Selectivity (%) | Yield (%) | Activity mmole glyoxylic acid mmole platinum min |
|---|---|---|---|---|---|
| VB1: 5% Pt/C | 5 | 89 | 58 | 52 | 16 |
| VB2: 2.5% Pt/C | 18 | 91 | 62 | 56 | 10 |
| VB3: 1% Pt/C | 80 | 77 | 69 | 53 | 5 |
| VB4: 5% Pt-5% Pb/C | 10 | 70 | 14 | 10 | 1.6 |
| BI: 5% PT-5% Mo/C | 3 | 83 | 70 | 58 | 30 |
| B2: 2.5% Pt-5% MO/C | 4 | 90 | 68 | 61 | 48 |
| B3: 1% Pt-5% MO/C | 75 | 80 | 65 | 52 | 5 |
| B4: 1% Pt-5% Ce/C | 65 | 50 | 80 | 40 | 5 |
| B5: 1% Pt-10% Ce/C | 120 | 85 | 72 | 61 | 4 |
| B6: 1% Pt-5% Ce/C | 3.5 | 90 | 73 | 66 | 29 |

VB: Reference example
B: Example

We claim:

1. A catalyst containing platinum on carbon as carrier for the catalytic oxidation of glyoxal to glyoxylic acid, characterized in that the catalyst also contains molybdenum and/or cerium in addition as modifiers and that platinum is present, relative to the carrier, in an amount of 0.1 to 5.0, preferably 0.5 to 3.5% by weight and the weight ratio between the platinum and the molybdenum and/or cerium present at the same time is 1:1 to 1:20, carbon and that the mixture is subsequently reduced at unchanged temperature by the addition of a reducing agent.

4. A method of producing glyoxylic acid by means of the oxidation of glyoxalic acid in an aqueous medium under the supplying of oxygen using a catalyst according to claim 1.

* * * * *